United States Patent [19]

Bernhardt

[11] Patent Number: 5,345,820

[45] Date of Patent: Sep. 13, 1994

[54] METHOD OF AND ARRANGEMENT FOR DETERMINING GEOHYDRAULIC PERMEABILITY OF GROUND REGIONS THROUGH WHICH GROUND WATER FLOWS

[75] Inventor: Bruno Bernhardt, Reutlingen, Fed. Rep. of Germany

[73] Assignee: IEG Industrie-Engineering GmbH, Reutlingen, Fed. Rep. of Germany

[21] Appl. No.: 29,823

[22] Filed: Mar. 11, 1993

[30] Foreign Application Priority Data

Mar. 11, 1992 [DE] Fed. Rep. of Germany ....... 4207692

[51] Int. Cl.⁵ .............................. E21B 47/00
[52] U.S. Cl. ................................... 73/155
[58] Field of Search ................. 73/155, 151, 38; 166/250

[56] References Cited

U.S. PATENT DOCUMENTS 3,181,608  5/1965  Palmer ................................ 73/155
3,550,445 12/1970  Kiel ..................................... 73/155
3,592,056  7/1971  Bermaix ............................. 73/155
3,604,256  9/1971  Prats ................................... 73/155
4,631,677 12/1986  Park et al. ........................... 73/155
4,969,111  6/1990  Merva ................................ 364/556
5,156,205 10/1992  Prasad ................................ 73/155

FOREIGN PATENT DOCUMENTS 0250279  12/1987  European Pat. Off. .
219881   3/1985   Fed. Rep. of Germany ........ 73/155
56-103350 8/1981  Japan .
2027910  2/1980   United Kingdom .

Primary Examiner—Robert J. Warden
Assistant Examiner—Krisanne M. Thornton
Attorney, Agent, or Firm—Michael J. Striker

[57] ABSTRACT

A measurement of geohydraulic permeability of ground regions is performed by producing a negative pressure in a well shaft and a measuring of the resulting raise or lowering of the ground water level in the well shaft without pumping out of ground water from the shaft.

18 Claims, 4 Drawing Sheets

METHOD OF AND ARRANGEMENT FOR DETERMINING GEOHYDRAULIC PERMEABILITY OF GROUND REGIONS THROUGH WHICH GROUND WATER FLOWS

BACKGROUND OF THE INVENTION

The present invention relates to a method of and arrangement for determining geohydraulic permeability of ground regions through which ground water flows, particularly for dimensioning a well providing a ground water circulation.

The determination of the geohydraulic permeability of ground regions is important for the dimensioning of wells which are produced in these ground regions. Depending on the degree of the permeability of the ground region, for example the depth and the diameter of the well shaft is determined as well as the selection of filter with which the well shaft is coated. It is especially important to provide the permeability determination for wells with a ground water circulation in the ground region which surrounds the well shaft. The range of the ground water circulation strongly depends on the geohydraulic permeability of the ground region as well as on its anisotrophy or in other words its different sizes and in different directions. Especially the ratio of the permeability in horizontal vertical direction to the permeability in the vertical flow direction is very important. Such wells providing a ground water circulation are utilized especially for removing contaminations in the ground region through which ground water flows. Only by the determination of the geohydraulic permeability of the contaminated ground region is it possible to preliminarily calculate how to dimension the well for covering the whole contaminated ground region and whether a second well is needed in some cases.

The geohydraulic permeability of ground has been determined by pumping tests. For this purpose wells are bored in the ground region to be investigated, and ground water is pumped out from them. By the pumping out, the ground water level in the surrounding area of the well shaft lowers. The degree of the lowering of the ground water level is determined by a level tube which is inserted in the ground at different distance from the well shaft. From the water quantity removed from the well shaft and the degree of lowering of the ground water level in the surrounding area of the well shaft the permeability of the ground can be determined. This known method has the disadvantage that it cannot be performed in cultivated areas since by the lowering of the ground water level also a lowering of the structures near the well shaft is possible. Moreover, since it is necessary to introduce level tubes in the surrounding area of the well shaft for measuring the lowering of the ground water level, the method is relatively expensive and requires a great measuring area. A further disadvantage is that the ground water withdrawn from the well shaft must be again supplied into the ground region. This must be performed at a certain distance from the well shaft for avoiding a falsification of the measuring results, which is very expensive.

SUMMARY OF THE INVENTION

Accordingly, it is an object of the present invention to provide a method of and an arrangement for determining geohydraulic permeability, which does not need pumping out of ground water and therefore eliminates related disadvantages.

In keeping with these objects and with others which will become apparent hereinafter, one feature of the present invention resides, briefly stated, in that in a well shaft in the ground region to be investigated above the ground water level a negative pressure of an adjustable magnitude is produced, the raise of the ground water level in the well shaft per unit time which results from this, as well as the negative pressure acting there and/or the lowering of the ground water level after elimination of the negative pressure are determined, and from these measuring values the geohydraulic permeability of the investigated ground region is calculated.

In contrast to the approach involving the pumping, no lowering but instead a raise of the ground water level in the surrounding area of the well shaft is produced here. The method therefore can be used in cultivated areas as well. Since no ground water is withdrawn from the well shaft, the problem of resupply of ground water into the ground is eliminated. Also no level tubes in the surrounding area of well shaft are needed for measuring the changes in the ground water level. The measurement of the changes of the ground water level is performed only in the well shaft. From the measured raise or lowering of the ground water level per unit time and the negative pressure acting in the well shaft, the hydraulic permeability of the ground can be determined at least as reliably as in the conventional pumping methods. The new method therefore provided a price-favorable, structurally simple, reliable and universally utilizable alternative to the measurements which use pumping steps.

The measurements can be performed after one another during flow of ground water from different direction in the well shaft and therefore the anisotrophy of the geohydraulic permeability of the ground region can be computed. In particular, it is possible to measure first the raise or the lowering of the ground water level during flow of ground water from the horizontal direction and then from vertical direction in the well shaft. In correspondence with the determined anisotrophy, then the dimensioning of a well to be formed in the investigated ground region can be performed. Also the horizontal permeability of the ground region at different depths can be measured. This is required especially for the dimensioning of wells with a ground water circulation, in which the well shaft is subdivided into two horizontal regions. From the permeability measurements at different depths, the required shaft depths and the favorable location for a partition for separating both shaft regions can be determined. If additionally the vertical permeability of the ground region is measured, the range of the well can be determined as well.

The arrangement for determination of geohydraulic permeability in accordance with the present invention has a well shaft with locally water permeable shaft wall while the well shaft above the ground water level is sealed in air and water impermeable manner, devices for producing a negative pressure and a measuring probe for measuring the change of the ground water level per time unit and the negative pressure acting in the shaft. The device for producing the negative pressure can include a suction pump, a vacuum chamber, and a valve and can be arranged outside the well shaft and connected with it through a tube. A predetermined negative pressure is first produced in the vacuum chamber by the suction pump and transmitted to the well shaft by opening of a valve. In this manner the negative pressure which acts in the shaft is easily adjustable from outside to the desired value. The measuring probes can be connected with an evaluating device located outside the well shaft, for reading or further processing of the received measuring values.

For measuring the horizontal geohydraulic permeability of the ground region to be investigated, the well shaft can have one or several horizontal regions with water permeable shaft wall which are sealed from one another. With several horizontal shaft regions, the upper shaft region or regions can be bridged by a pipe which extends through the seals between the regions to the height above the water level in the well shaft. In this way the permeability measurements can be performed one after the other during the flow of ground water into different depths in the well shaft. Thereby available layers with different water permeability in ground can be determined. For measurement of the vertical geohydraulic permeability of the ground region to be investigated, the well shaft can be formed by a downwardly open tube which is driven in the ground region and has an interior which is free only in the region of ground located above the ground water level. In this manner, ground water is aspirated exclusively by the lower tube opening in the well shaft filled with ground and must flow in vertical direction through the ground located there. A horizontal flow of the ground water is impossible, and therefore the measurement of the vertical permeability of the ground is very accurate. The tube can have a small diameter and can be driven on or screwed in the ground region to be investigated.

Another possibility of measurement of the vertical permeability involves the formation of the well shaft composed of three concentric tubes. The central tube has at its lower end a cutting tool and is connected at its upper end with a rotary drive, while the inner tube together with the bore core is removable from the central tube. The three tubes are bored by means of the central tube to the ground water level in the ground. Subsequently, the inner tube with the bore core in it is withdrawn from the central tube, released from the bore core and again inserted into the central tube. Then the whole arrangement is bored into the ground to the desired depth, and the inner and the outer tubes are used as supporting tubes for the central tube which drives the arrangement by the rotary drive into the ground. For facilitating the boring process, a device for pressing in of rinsing water into the chamber between the tubes can be provided, for washing out of ground released during the boring process.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
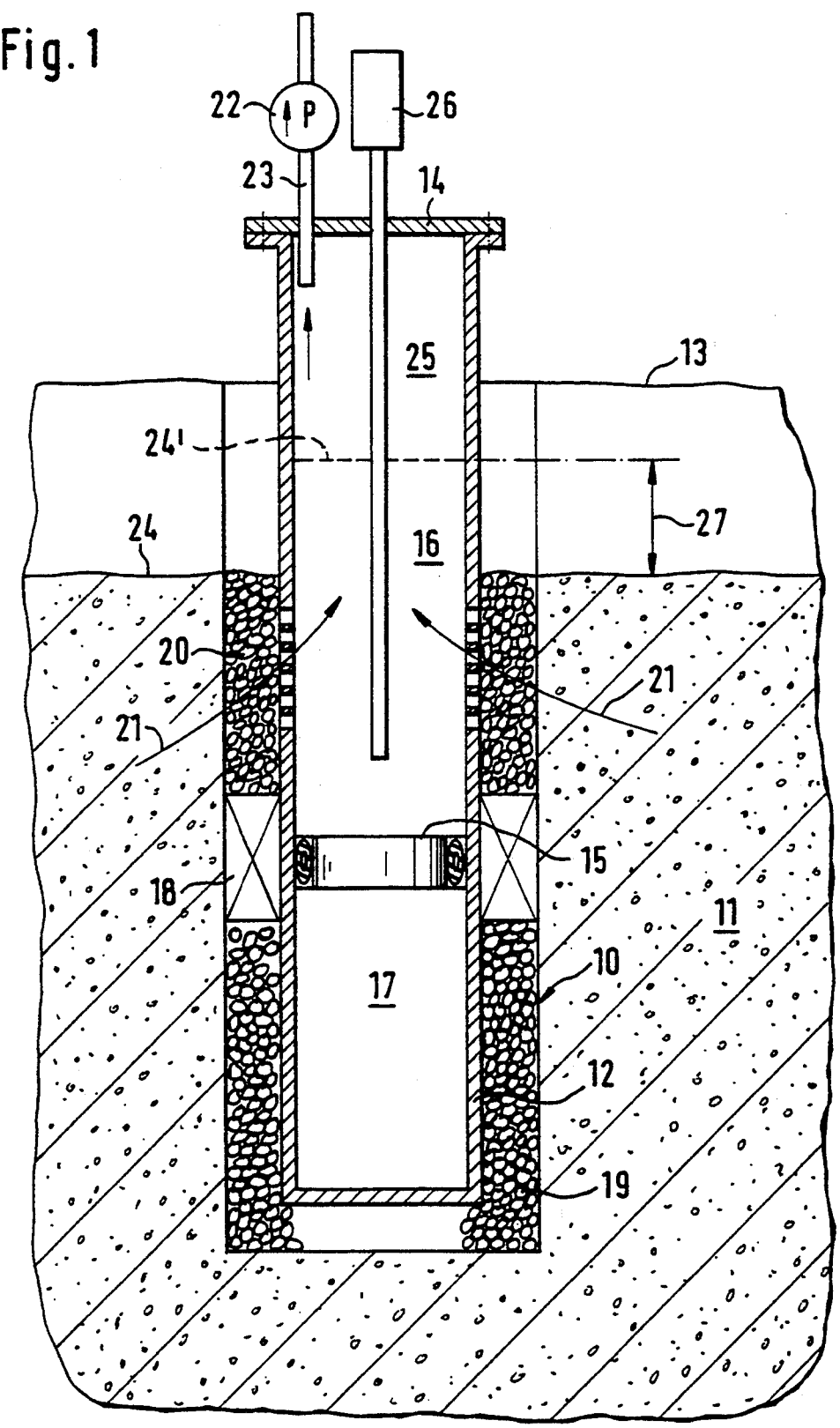
FIG. 1 is a view showing a longitudinal section of an arrangement for determining geohydraulic permeability in accordance with a first embodiment of the invention.

As can be seen from FIG. 1 a well shaft 10 is driven to a ground region 11 through which ground water passes and whose geohydraulic permeability must be determined. The shaft 10 is coated with a tube 12. The tube 12 is closed with a cover 14 above a ground surface 13 and subdivided by a partition 15 into an upper region 16 and a lower region 17. At the height of the partition 15, the tube 12 is surrounded by a sealing pack 18. A filter gravel 19 surrounds the tube 12 in remaining regions. In the upper shaft region 16 the tube 12 has water passage openings 20 for flowing the ground water into the interior of the shaft as identified by arrows 21. A suction pump 22 is arranged outside the well shaft 10 and connected through a pipe 23 with a region 25 of the tube 12 located above the ground water level 24. A negative pressure is produced in the region 25 by the suction pump 22. Thereby the ground water level in the well shaft 10 raises relative to the stationary level 24 to a level 24'. This raise of the ground water level, as well as the negative pressure acting in the region 25, is measured by a measuring probe 26 extending from outside through the cover 14 to the shaft region 16. Instead of the measurement of the raise of the ground water level or additionally to this measurement, also a measurement of the further lowering of the ground water level per unit time can be performed. From these measuring values the geohydraulic permeability of the ground 11 can be computed. With the arrangement shown in FIG. 1, substantially the permeability of the ground 11 in horizontal direction in the direction of the water passage openings 20 in the upper shaft region 16 is determined.

Figure 2:
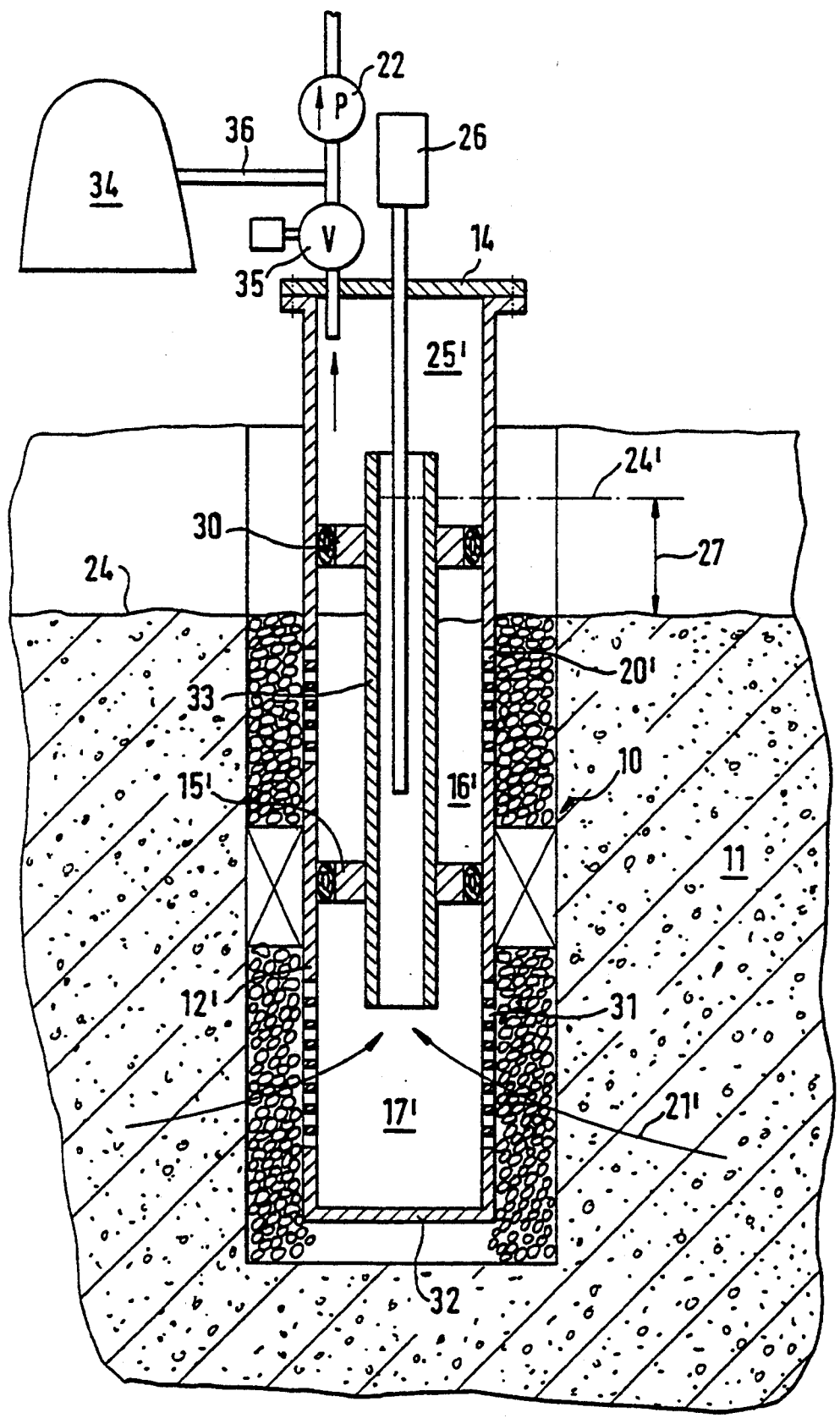
FIG. 2 is a view showing a longitudinal section of an arrangement for determining geohydraulic permeability in accordance with a second embodiment of the invention.

FIG. 2 shows an arrangement for measuring the horizontal permeability of the ground 11 at two different depths. Also here the shaft 10 is covered with a tube 12' which however is separated by two partitions 15' and 30 into three regions 17', 16' and 25'. In contrast to the arrangement of FIG. 1, the tube 12' has water passage openings 20' and 31 in two different shaft regions, namely in the regions 16' and 17'. The lower end of the tube is closed by a bottom plate 32 and the upper end located above the ground surface 13 is closed by a cover 14. Since the tube 12' is provided with the water passage openings 20' and 31 at two different depths, the permeability of the ground 11 can be measured at two different depths. In FIG. 2 the measurement of the permeability in the depth of the ground region corresponding to the lower shaft region 17' is illustrated. For this purpose, the upper shaft region 16' is overlapped by a tube 33 which extends through both partitions 30 and 15' from the shaft region 25' above the ground water level 24. Outside the shaft 10, a suction pump 22 for producing negative pressure in the shaft 10 is arranged. A predetermined negative pressure is produced for this purpose first in a vacuum chamber 34 by the suction pump 22, before it is transmitted by opening of a valve 35 to a connecting conduit 36 between the vacuum chamber 34 and the well shaft 10 to the well shaft. The negative pressure in the shaft 10 provides an increase of the ground water level from the stationary level 24 to an increased level 24'. This increase of the water level is produced exclusively by ground water which flows into the shaft region 17' as identified with the arrow 21'. Due to the overlapping of the region 16' with the tube 33, the negative pressure in this shaft region is not noticeable. The increase of the ground water level to the level 24' is thereby determined only in the tube 33, and the change of this increase 27 per unit time is detected by a measuring probe 26. From these measuring values and the known negative pressure in the shaft 10, it is possible to compute the geohydraulic permeability of the ground 11 at the depth corresponding to the shaft region 17' in a horizontal direction. When the horizontal geohydraulic permeability of the ground 11 at a depth, which corresponds to the shaft region 16' must be measured, the partition 30 and the throughgoing tube 33 are removed from the well shaft. The negative pressure produced in the shaft region 25' acts then only on the upper region 16' of the shaft, so that the water can flow exclusively through the passage openings 20' in the tube 12' into the interior of the shaft. The measuring device corresponds to the device of FIG. 1.

Figure 3:
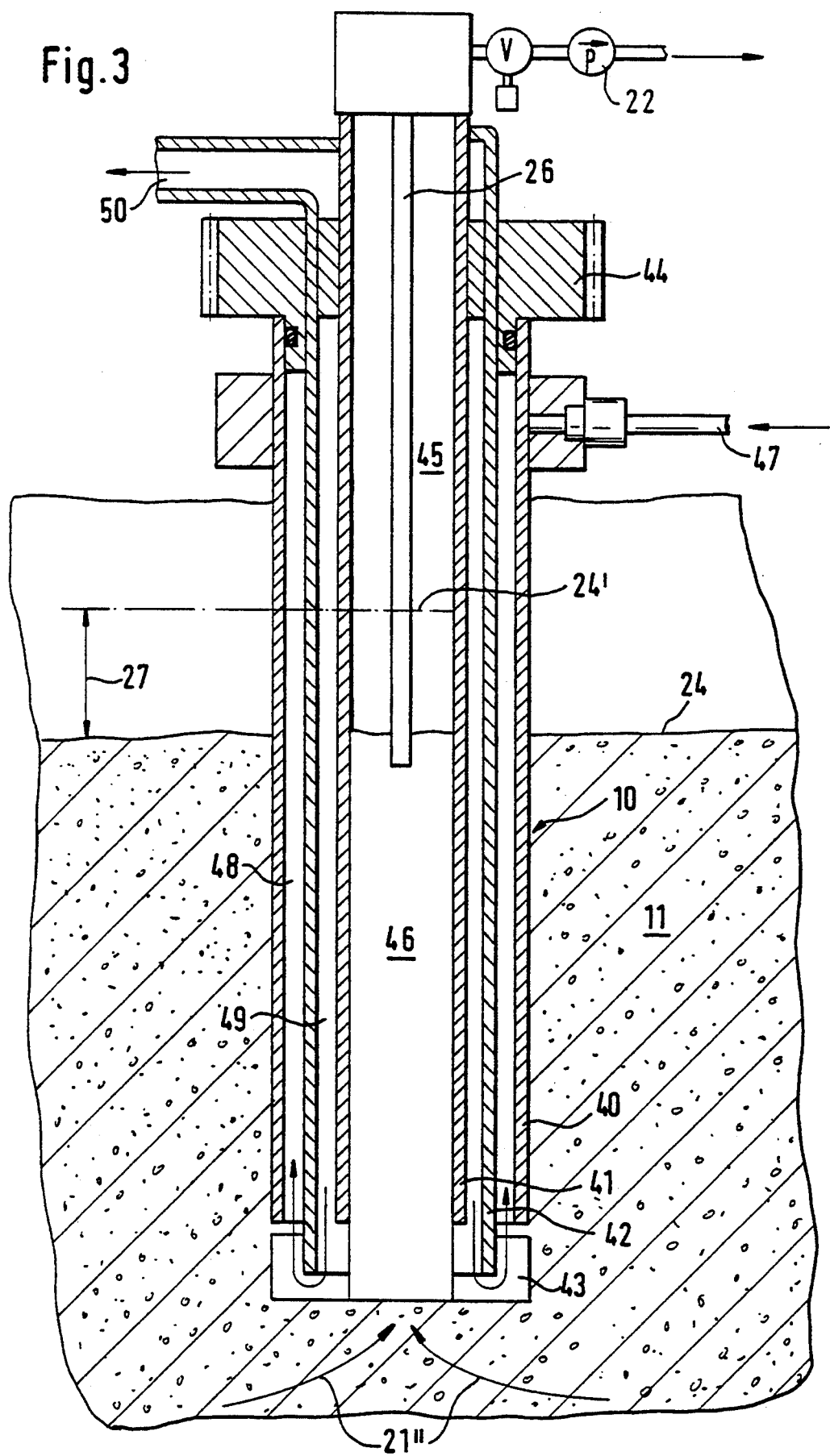
FIG. 3 is a view showing a longitudinal section of an arrangement for determining geohydraulic permeability in accordance with a third embodiment of the invention.

FIG. 3 shows an arrangement for measuring the vertical geohydraulic permeability of the ground 11. The well shaft 10 is formed by three concentric tubes including an outer supporting tube 40, an inner supporting tube 41 and a central bore tube 42. The bore tube 42 is provided at its lower end with a cutting tool 43. At its upper end a toothed rim 44 is arranged for driving the tube 42. The interior of the shaft 10 is released from ground only in a region 45 above the stationary ground water level 24. This is obtained in that, during boring of the arrangement in the ground 11, upon reaching the water level 24 the inner supporting tube 41 together with the bore core from the ground is withdrawn from the central tube 42. Then the tube 41 is again inserted and the whole arrangement is further driven to the desired depth by boring with the central tube 42 in the ground 11. In the region 45 of the shaft 10 a negative pressure is produced by a suction pump 22. It provides a raise of the water level to a level 24' in the interior of the shaft, and this raise is activated by flowing of the ground water from below into the inner tube 41 as identified by arrows 21'. The water must flow to the bore core of ground available in the lower shaft region 46. By measuring the negative pressure produced in the shaft region 45 as well as the raise 27 of the ground water level 24 or its lowering per unit time by means of a measuring probe 26, the vertical geohydraulic permeability of the ground 11 can be measured. For facilitating the boring process of the bore tube 42, rinsing water can be pumped through an opening 47 into the intermediate tubular chambers 48 and 49, with the ground which is released by the cutting tool 43, and rinsed out through an output 50.

Figure 4:
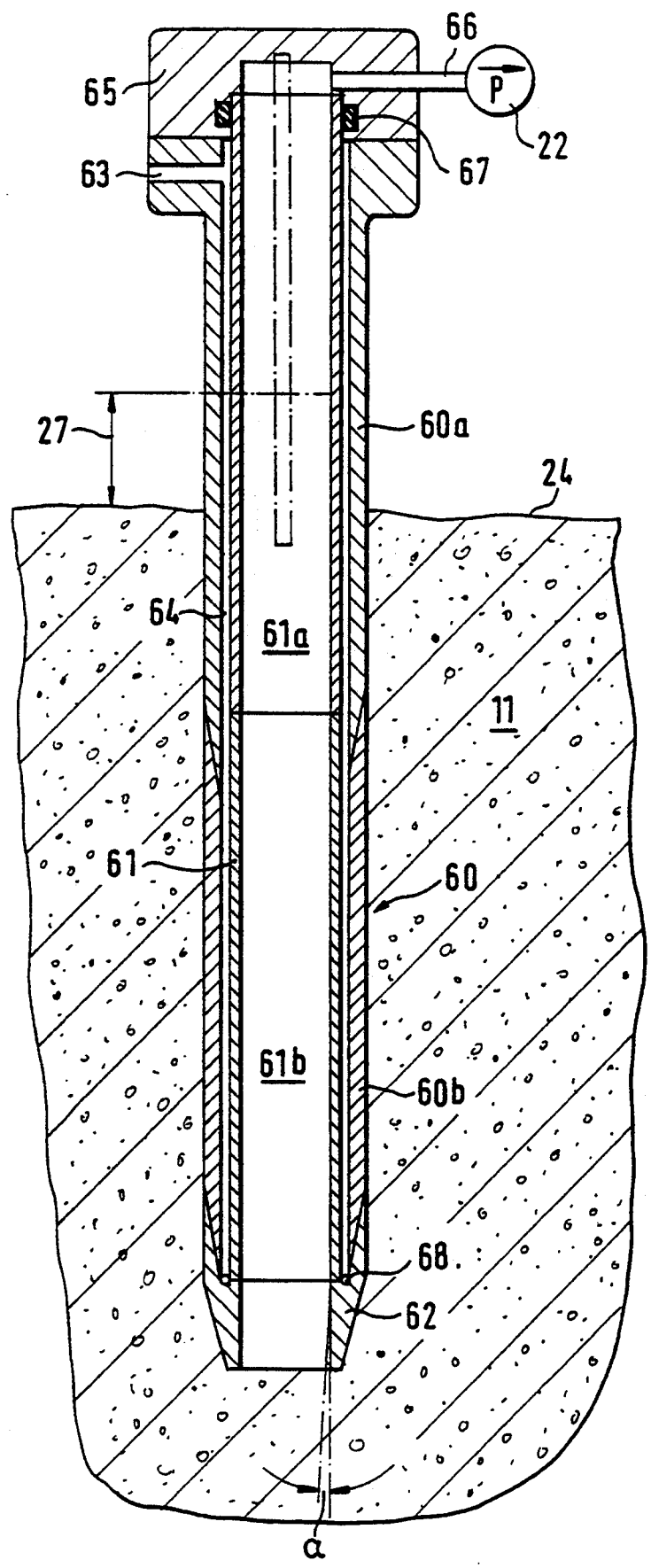
FIG. 4 is a view showing a longitudinal section of an arrangement for determining geohydraulic permeability in accordance with a fourth embodiment of the invention.

FIG. 4 shows a second embodiment of an arrangement for measuring the vertical permeability. In an outer level tube 60, a transparent inner tube 61 is removably arranged. The level tube 60 is composed of tube elements 60a and 60b which are screwed with one another. At the lower end it is provided with a hardened and injection molded end piece 62 for facilitating the driving of the tube 60 into the ground 11. The level tube 60 can also have an outer thread for driving in the ground 11. The end piece 62 extends on the inner tube under a small angle α conically inwardly for avoiding an increased radial pressure of the core onto the inner tube. It can also be provided with an outer thread for facilitating of screwing the arrangement into the ground. The inner tube 61 which is located downwardly on the end piece 62 of the level tube 60 and sealed by sealing rings 67 and 68 against the level tube 60, can be also composed of tubular elements 61a and 61b which are welded with one another. Due to the transparency of the inner tube 61 the non-destroyed bore core which is removed with it can be easily optically found and conclusions as to the composition of the ground 11 can be made. On the upper end the level tube 60 has a ventilating opening 63 for the free space 64 located between the tubes 60 and 61, in order to eliminate the formation of negative pressure during pulling out of the inner tube 61 from the level tube 60 and a cover 65 on which a measuring probe 26 is arranged. A tube 66 leads through the cover 65 to a suction pump 22 for producing negative pressure in the arrangement.

It will be understood that each of the elements described above, or two or more together, may also find a useful application in other types of methods and constructions differing from the types described above.

While the invention has been illustrated and described as embodied in a method of and an arrangement for determination of geohydraulic permeability of ground regions through which ground water flows, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of determining geohydraulic permeability of ground regions through which ground water flows for dimensioning of a well providing ground water circulation, the method comprising the steps of producing a negative pressure of an adjustable magnitude above a ground water level in a well shaft in a ground region to be investigated; measuring a raise of the water level produced by the negative pressure in the well shaft per unit time and also measuring at least one of the negative pressure acting in the well shaft and lowering of the ground water level per unit time after elimination of the negative pressure to obtain respective measuring values; and determining a geohydraulic permeability of the ground level to be investigated from the obtained measuring values.

2. A method as defined in claim 1, wherein said measuring of the raising or lowering of the ground water level is performed during flowing of ground water from different directions into the well shaft per unit time, said determining includes determining anisotrophy of the geohydraulic permeability of the ground region from the measuring values during the flow of the ground water from different directions in the well shaft per unit time.

3. A method as defined in claim 2, wherein said measuring of the raising or lowering of the ground water level during flow of the ground water is performed during flow of the ground water from a horizontal direction and from a vertical direction into the well shaft.

4. A method as defined in claim 2, wherein said measuring of the raising or lowering of the ground water level during flow of the ground water is performed by measuring during flow of the ground water from a horizontal direction at different depths.

5. An arrangement for determining geohydraulic permeability of ground regions through which ground water flows for dimensioning wells for producing a ground water circulation, the arrangement comprising a locally water permeable shaft wall defining a well shaft which is air- and water-impermeably closed above a ground water level; means for producing a negative pressure in the well shaft above the ground water level in the shaft; and a measuring probe for measuring a change of the ground water level produced by the negative pressure per unit time in the well shaft and also for measuring the negative pressure acting in the well shaft to obtain respective measuring values so as to determine the geohydraulic permeability from the obtained measuring values.

6. An arrangement as defined in claim 5, wherein said means for producing a negative pressure include a suction pump, a vacuum chamber and a valve, said means for producing negative pressure being located outside the well shaft and connected with the well shaft; and further comprising means for connecting said means for producing negative pressure with said well shaft.

7. An arrangement as defined in claim 6, wherein the connecting means includes a tube which connects said means for producing negative pressure with the well shaft.

8. An arrangement as defined in claim 5; and further comprising an evaluating device located outside the well shaft and connected with the measuring probe.

9. An arrangement as defined in claim 5, wherein said shaft wall has a plurality of water permeable shaft wall portions which correspond to a plurality of horizontal regions of the well shaft and which are sealed relative to one another.

10. An arrangement as defined in claim 9; and further comprising means for sealing the water permeable shaft wall regions from one another.

11. An arrangement as defined in claim 9; and further comprising a tube which overlaps at least one upper shaft region and extends through said means for sealing to the ground water level in the well shaft.

12. An arrangement as defined in claim 5; and further comprising at least one upwardly open tube extending in ground and forming the well shaft for measuring a vertical geohydraulic permeability of the ground region to be investigated, said tube having an interior which does not have ground only in a region located above the ground water level.

13. An arrangement as defined in claim 12, wherein said at least one tube is introducible into the ground region to be investigated.

14. An arrangement as defined in claim 5, wherein the well shaft for measuring a vertical geohydraulic permeability of the ground region to be investigated is formed by two concentric tubes including an inner tube composed of a transparent flexible material and having a lower end, and an outer tube having a hardened, tipped end piece on which said lower end is arranged.

15. An arrangement as defined in claim 14, wherein said inner tube and said outer tube form a ventilatable free space therebetween.

16. An arrangement as defined in claim 14, wherein said inner tube is composed of tube pieces which are welded together, said outer tube having an outer thread for boring into the ground.

17. An arrangement for determining geohydraulic permeability of ground regions through which ground water flows for dimensioning wells for producing a ground water circulation, the arrangement comprising a locally water permeable shaft wall which defines a well shaft, which is air-and water-impermeably closed above a ground water level; means for producing a negative pressure in the well shaft; and a measuring probe for measuring change of the ground water level per unit time and the negative pressure acting in the shaft so as to determine the geohydraulic permeability from thusly measured values, said well shaft being formed by three concentric tubes including a central tube provided having a lower end provided with a cutting tool and an upper end connectable with a rotary drive, an inner tube which together with a bore core is removable from said central tube and an outer tube.

18. An arrangement as defined in claim 17; and further comprising means for pumping rinsing water into a space between said tubes for washing out of ground released during boring.

* * * * *